United States Patent
Kuai et al.

(10) Patent No.: US 10,036,712 B2
(45) Date of Patent: Jul. 31, 2018

(54) DEFECT INSPECTION SYSTEM AND METHOD USING AN ARRAY OF LIGHT SOURCES

(71) Applicant: PHILIPS LIGHTING HOLDING B.V., Eindhoven (NL)

(72) Inventors: Shuguang Kuai, Shanghai (CN); Mark Christoph Jaeger, Veldhoven (NL); Weixi Zhou, Shanghai (CN)

(73) Assignee: PHILIPS LIGHTING HOLDING B.V., Eindhoven (NL)

( * ) Notice: Subject to any disclaimer, the term of this patent is extended or adjusted under 35 U.S.C. 154(b) by 172 days.

(21) Appl. No.: 15/029,472

(22) PCT Filed: Oct. 13, 2014

(86) PCT No.: PCT/EP2014/071826
§ 371 (c)(1),
(2) Date: Apr. 14, 2016

(87) PCT Pub. No.: WO2015/058982
PCT Pub. Date: Apr. 30, 2015

(65) Prior Publication Data
US 2016/0266046 A1    Sep. 15, 2016

(30) Foreign Application Priority Data

Oct. 24, 2013    (WO) ............... PCT/CN2013/001283
Dec. 2, 2013    (EP) ........................... 13195318

(51) Int. Cl.
*G01N 21/88*    (2006.01)
*H04N 5/225*    (2006.01)

(52) U.S. Cl.
CPC ..... *G01N 21/8806* (2013.01); *G01N 21/8803* (2013.01); *H04N 5/225* (2013.01); *G01N 2021/8809* (2013.01); *G01N 2201/0633* (2013.01); *G01N 2201/12* (2013.01)

(58) Field of Classification Search
CPC .......... G01N 21/8806; G01N 21/8803; G01N 2021/8809; G01N 2021/0633; G01N 2021/12; H04N 5/225
USPC ...................................................... 348/128
See application file for complete search history.

(56) References Cited

U.S. PATENT DOCUMENTS

| | | | |
|---|---|---|---|
| 4,918,321 A | | 4/1990 | Klenk et al. |
| 4,920,385 A | * | 4/1990 | Clarke .................. G01N 21/88 356/237.2 |
| 5,237,404 A | * | 8/1993 | Tanaka ................. G01B 11/303 348/128 |

(Continued)

FOREIGN PATENT DOCUMENTS

| | | |
|---|---|---|
| EP | 1832867 A1 | 12/2007 |
| EP | 2693167 A2 | 5/2014 |

(Continued)

*Primary Examiner* — Jay Patel
*Assistant Examiner* — Marnie Matt

(57) ABSTRACT

A defect inspection system is provided for inspection of defects in the surface of a sample. An array of light sources is used, with different light sources providing light to the sample from different directions. A main direction of illumination is defined with highest intensity, and this direction evolves over time. By providing varying directional illumination instead of blanket illumination, it becomes easier to detect defects.

13 Claims, 6 Drawing Sheets

(56) References Cited

U.S. PATENT DOCUMENTS

| | | | | |
|---|---|---|---|---|
| 5,248,919 | A | * | 9/1993 | Hanna ................ H05B 39/086 |
| | | | | 315/291 |
| 5,636,024 | A | | 6/1997 | Crookham et al. |
| 6,100,990 | A | * | 8/2000 | Ladewski .............. G01N 21/55 |
| | | | | 356/124 |
| 6,525,331 | B1 | * | 2/2003 | Ngoi ................. G01N 21/8806 |
| | | | | 250/237 G |
| 6,788,411 | B1 | | 9/2004 | Lebens |
| 7,525,669 | B1 | * | 4/2009 | Abdollahi .......... G01B 11/2522 |
| | | | | 356/603 |
| 2002/0009218 | A1 | * | 1/2002 | Chapman ............... G01N 21/88 |
| | | | | 382/141 |
| 2005/0248555 | A1 | * | 11/2005 | Feng ................... G09G 3/3426 |
| | | | | 345/204 |
| 2009/0268965 | A1 | * | 10/2009 | Mita ..................... G01B 11/25 |
| | | | | 382/190 |
| 2013/0057678 | A1 | | 5/2013 | Prior Carrillo et al. |
| 2013/0293879 | A1 | * | 11/2013 | Honda ................ G01N 21/956 |
| | | | | 356/237.4 |
| 2015/0242445 | A1 | * | 8/2015 | Prado ..................... G04F 13/02 |
| | | | | 348/207.1 |
| 2016/0097725 | A1 | * | 4/2016 | Porter ............... G01N 21/8803 |
| | | | | 356/237.2 |

FOREIGN PATENT DOCUMENTS

| | | |
|---|---|---|
| WO | 2006109258 A1 | 10/2006 |
| WO | 2011144964 A1 | 11/2011 |

* cited by examiner

DEFECT INSPECTION SYSTEM AND METHOD USING AN ARRAY OF LIGHT SOURCES

CROSS-REFERENCE TO PRIOR APPLICATIONS

This application is the U.S. National Phase application under 35 U.S.C. § 371 of International Application No. PCT/EP2014/071826, filed on Oct. 13, 2014, which claims the benefit of PCT Application No. PCT/CN2013/001283, filed on Oct. 24, 2013 and European Patent Application No. 13195318.4, filed on Dec. 2, 2013. These applications are hereby incorporated by reference herein.

FIELD OF THE INVENTION

This invention relates to a defect inspection system and method, for lighting a sheet material sample to enable detection of surface defects in the sample.

BACKGROUND OF THE INVENTION

It is known to illuminate sheet material samples to enable inspection for flaws in the surface.

One particular example is for painted surfaces, such as for example automobile bodies, where the paint or the underlying surface is inspected for flaws. Most automobile manufacturers use robotics and an automated painting system to apply various coats of paint to create the paint surface on the automobile bodies that are then used to create the complete automobile. While such systems generally perform satisfactorily, most manufacturers have a quality review of the paint job prior to approving the painted car body for assembly into the completed car.

The quality control can be based on manual visual inspection or automated image processing of images captured by cameras.

A manual inspection process typically involves workers manually moving around each automobile body as it moves along a conveyor and visually scanning the automobile body for a number of different possible flaws.

The workers are generally given only a short time (for example only several minutes) to evaluate the entire automobile body. Generally, there is a paint inspection station that has sufficient room for the workers to walk around each car body. The standard approach is to provide as much direct light as possible to the car bodies during the inspection process, based on the understanding that the more light, the easier it is to visually identify flaws. The emphasis is on lighting the car body.

The inspection workers must watch for as many as several tens of different types of flaws or defects. For example, if there is an underlying flaw such as a raised portion or recessed portion in the car body metal, this will normally be reflected in a raised or recessed portion respectively in the paint job. Also, such things as dust or other particles that may have settled on the car body prior to or during painting will result in a noticeable flaw.

Presently, automobile paint jobs are multi-coat. For example, a first coat or a neutral color rust inhibitor of fairly matte finish (sometimes called an "E" coat), is applied to the metal. A primer coat, usually neutral with a somewhat matte finish or the same color as the ultimate car color, is applied to the first coat. Finally, one or more top coats, for example, a base coat plus a clear coat can be applied over the primer coat.

The first coat is generally inspected for uniformity, flaws and foreign materials. The primer coat is analyzed for flaws, evenness, uniformity, dirt, cavities, runs, and negative or positive depressions in the metal. The top coat creates a highly reflective surface which is inspected for such things as evenness, white spots, striations, swirl marks and other flaws.

If a flaw is identified, the workers attempt to polish it out on the spot, or the car body must be towed from the assembly line to another location for paint repair.

Providing a good lighting solution can help workers in the car factories to detect the defects early and effectively. However, the current approach of bathing the car body in light is not found to be ideal, and workers sometime rely on their hands rather than eyes to detect defects on car body.

SUMMARY OF THE INVENTION

The invention is defined by the claims.

According to a first aspect of the invention, there is provided a defect inspection system for manual visual inspection of surface defects in a sample, comprising:

a lighting system for illuminating the sample surface comprising an array of light sources formed within a plane, wherein the array of light sources defines a range of illumination directions towards the sample within the plane, which range covers at least 90 degrees; and a controller for controlling the light sources to operate in a sequence such that each point of the sample is illuminated in a sequence with a maximum light source intensity in a single incident direction, and over time the direction in which the maximum light source intensity is provided changes to cover said range.

According to a second aspect of the invention, there is provided a defect inspection system for automated inspection of surface defects in a sample, comprising:

a lighting system for illuminating the sample surface, comprising an array of light sources formed within a plane, wherein the array of light sources defines a range of illumination directions towards the sample within the plane, which range covers at least 90 degrees; and a controller for controlling the light sources to operate in a sequence such that each point of the sample is illuminated in a sequence with a maximum light source intensity in a single incident direction, and over time the direction in which the maximum light source intensity is provided changes to cover said range;

at least one camera;

a controller for controlling the camera to take successive images during the light source operation sequence; and a processor for processing the images to derive at least one difference image, wherein the difference image highlights changes in shadow position caused by randomly located surface defects on an otherwise smooth surface, and to provide defect detection based on the difference image.

In both aspects, the sample preferably comprises a sheet material, or an object with a sheet surface, which is intended to have a smooth surface (which may be a flat plane or a smoothly curved surface), but which may have randomly located surface defects at which the smoothness of the surface is disrupted. The lighting system results in shadows being formed by these surface defects. The changes in shadow positions resulting from the change in illumination direction can then be easily identified.

They may be identified visually in a manual visual inspection system, or they may be identified by image processing based on identifying differences in captured images. These image differences result from changes in the directions in which shadows are cast. In the automated approach, one or more difference images can be used to detect defects. The appearance of defects changes for different lighting conditions within the sequence, whereas a defect-free surface has a much smaller change in image. Thus, by comparing one or more difference images with a threshold, it is possible to detect defects automatically.

In both aspects, the invention provides a system in which the positions of shadows cast by surface defects are used to identify those surface defects. By providing a moving direction of principal illumination, the shadows cast will move over time which makes the defects easier to identify either manually or using cameras.

The plane of light sources can form a gantry around the sample to be analysed (in known manner), with the light sources all directed inwardly to illuminate the sample. However, instead of simply illuminating all light sources at once and at the same intensity to flood the sample with light, directional lighting is provided which evolves over time. In this way, all locations on the sample are illuminated by a lighting which has principal direction in which the intensity is higher than for all other directions, and this principal direction evolves over time. It has been found that defects are more easily observed by means of directional lighting in a particular direction or range of directions.

The invention enables the visibility of defects to be improved, for example on car body surfaces, so that workers can find defects more easily and more effectively.

The range of angles will depend on the nature of the sample. For a single flat surface a range of 90 degrees may be suitable. For a more 3-dimensional object, for example with sides and a top or bottom, a larger range is appropriate, such as at least 135 degrees or even at least 180 degrees (which corresponds to a gantry surrounding an object from a ground plane up).

The controller can be adapted to control the light source array to turn on one light source to a set brightness and turn off or dim the others in sequence. This provides a most basic approach, in which at any time the parts of the sample illuminated by the activated light source receive direct light only or principally from one direction (either because the light source is a point source or a collimated source). However, this can result in a long inspection process.

Therefore, in a preferred arrangement, the controller is adapted to control the light source array to vary the intensity of the output of the light sources, such that each light source has a greater intensity than the others at respective points in time within the sequence.

This approach can provide a smooth dynamic change in the lighting distribution. The detectability of defects is improved by having principal lighting from different angles at different times. The change in intensity of the light sources can follow a sequence. This sequence enables different defects to become visible from the general background at different times, and the chance to detect defects is increased. By way of example, the light sources can be illuminated with sinusoidal intensity profiles, all with the same period but different phases. This maintains a high level of general illumination so that all areas of the sample can be inspected, but with a primary illumination direction which evolves over time.

The array of light sources can comprise a plurality of sub-arrays of light sources, each sub-array formed within a respective plane, the planes for different sub-arrays being parallel or near parallel, so that the normal directions are in a line (which may be straight or curved). This can for example define a series of lighting gantries.

The system preferably comprises a sample platform, wherein the sample platform is movable relative to the lighting system in a direction perpendicular to the plane. The (or each) array of light sources provides illumination in their plane but can also provide illumination forward and backward along the movement axis, so that the illuminated regions overlap. The movement can be continuous or step-wise.

The system can comprise a car body panel paintwork inspection system. By way of example, the car can be advanced through the inspection area at a relatively slow speed, for example 5 cm/s. The lighting intensity can change with a period of around 6 s.

However, the invention can be applied to any inspection system for a sample with a smooth surface to be inspected. The sample can be sheet material, or a solid body required to have a smooth surface finish.

The invention also provides a method of providing lighting to a surface of a sample to enable visual manual inspection of defects in the sample, the method comprising:

illuminating the sample surface using an array of light sources formed within a plane, wherein the array of light sources defines a range of illumination directions towards the sample within the plane, which range covers at least 90 degrees; and controlling the light sources to operate in a sequence such that at any point in time each illuminated point of the sample is illuminated by direct light from the light source array in which a maximum light source intensity is provided in a single incident direction, and over time the incident direction at which the maximum light source intensity is provided changes to cover said range.

The invention also provides a method of providing lighting to a surface of a sample to enable automated inspection of defects in the sample, the method comprising:

illuminating the sample surface using an array of light sources formed within a plane, wherein the array of light sources defines a range of illumination directions towards the sample within the plane, which range covers at least 90 degrees; and controlling the light sources to operate in a sequence such that each point of the sample is illuminated in a sequence with a maximum light source intensity in a single incident direction, and over time the direction in which the maximum light source intensity is provided changes to cover said range;

taking successive camera images during light source operation sequence;

processing the images to derive at least one difference image wherein the difference image highlights changes in shadow position caused by randomly located surface defects on an otherwise smooth surface; and providing defect detection based on the difference image.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a defect inspection system for inspection of defects in a sheet material sample. An array of light sources is used, with different light sources providing light to the sample from different directions. A main direction of illumination is defined with highest intensity, and this direction evolves over time. By providing varying directional illumination instead of blanket illumination, it becomes easier to detect defects. In particular, the way shadows are cast changes for different illumination directions. This gives an evolving image which is easier to detect either during visual inspection or based on an automated system which processes captured camera images.

Figure 1A:
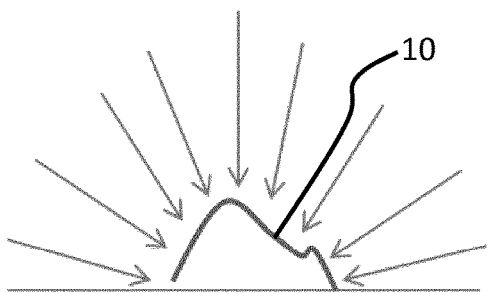
FIG. 1 shows a defect illuminated from all directions and a defect illuminated from one direction, and shows how the single direction illumination gives improved defect detection.
Figure 1A:
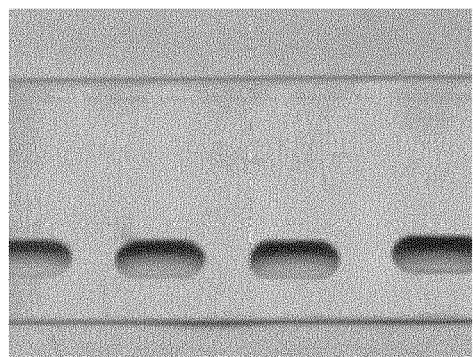
Figure 1B:
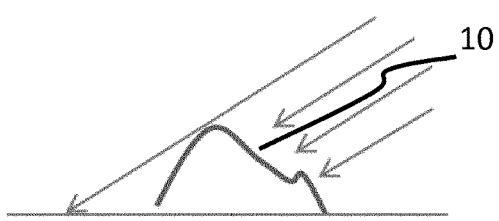
Figure 1B:
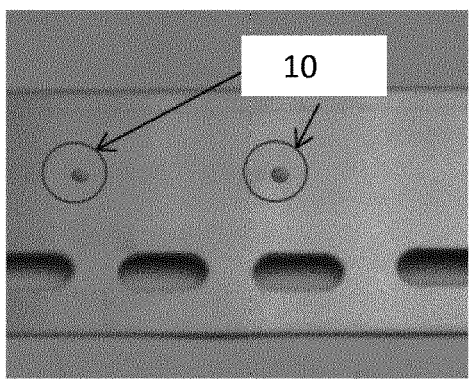

FIG. 1(a) shows a defect 10 illuminated from all directions. This gives a low contrast when viewed from a given direction (e.g. above). FIG. 1(b) shows the same defect 10 illuminated from one direction. The images show how the single direction illumination gives improved defect detection.

Thus, it can be seen that providing directional lighting can significantly enhance defect contrast. The typical lighting solution, offering light from all directions, is thus not an optimal condition to improve the contrast of defects and background because it cannot create a strong shadow of these defects. In contrast, providing light from a certain direction can enhance contrast to render the defect more strongly visible.

FIG. 2 shows how different types of defect can most easily be detected from different illumination directions.

Figure 2A:
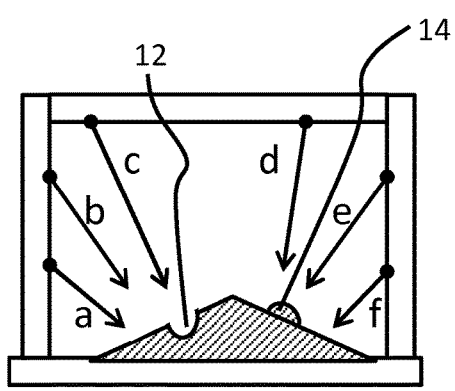
FIG. 2 shows how different types of defect can most easily be detected from different illumination directions.
Figure 2B:
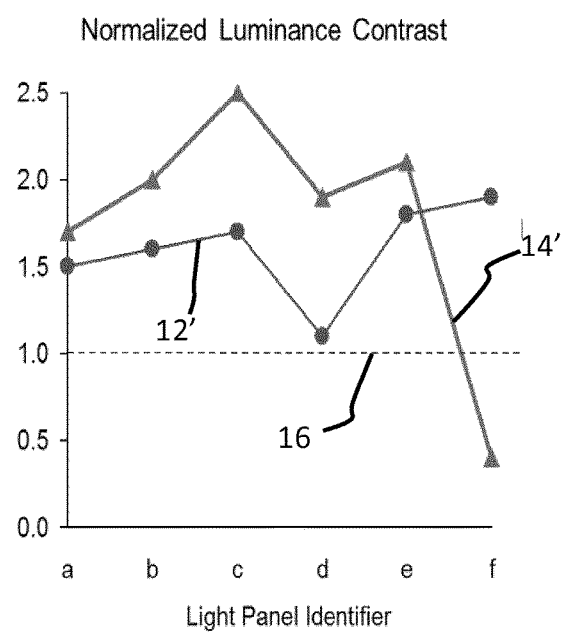

FIG. 2(a) shows a sample with two defects; an indentation 12 and a raised bump 14. Six illumination directions are defined, shown as "a" to "f". FIG. 2(b) shows a measure of luminance contrast (carried out as an experiment) for these defects and based on the six different illumination directions. Plot 12' shows the contrast for the indentation, plot 14' shows the contrast for the bump and plot 16 shows the reference contrast based on all lights being turned on.

It can be seen that the contrast of the defect when all lights on is not highest. Offering light from specific directions results in a higher contrast created by those defects. Furthermore, for different types of defect, the best lighting conditions are different. FIG. 2(b) shows that for the indentation 12, the direction "c" provides the best contrast whereas direction "f" provides the best contrast for the bump.

For a real sample, the shape and locations of defects are random and unpredictable, so a fixed lighting condition is not able to optimize the defect detection for all defect types.

To improve the visibility of different types of defects, the lighting system of the invention systematically changes the lighting distribution on the sample.

Figure 3:
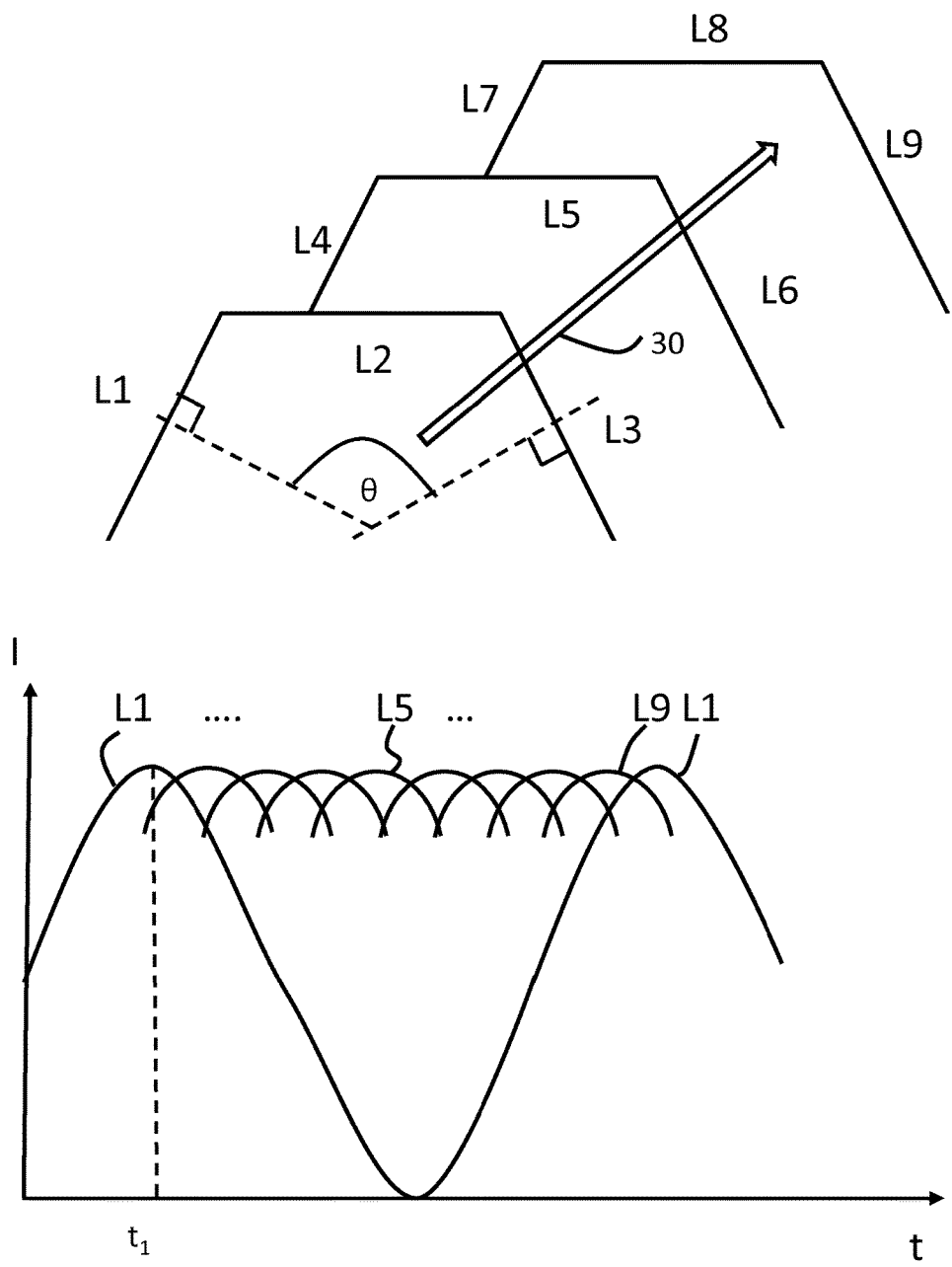
FIG. 3 shows an example of lighting array for use in the system of the invention and associated timing.

FIG. 3 shows an example of lighting array for use in the system of the invention and associated timing.

In a simplest implementation, there is a single arch of light sources providing light to the sample. However, FIG. 3 shows three arches, each with three light sources. The nine light sources in total are numbered L1 to L9.

Each arch comprises a sub-array of light sources formed within a plane. The light sources emit light inwardly towards the sample positioned within the arch. In the example shown, the light sources are each in the form of a strip, which emits substantially collimated light (as shown in FIG. 1(b)) so that there is essentially a single direction of illumination. Note that a non-collimated point light source can also provide direct light inwardly such that any point on the sample again only receives light in a single direction (i.e. along the vector between the point light source and the respective point on the sample).

The array of light sources defines a range of illumination directions towards the sample. The size of this range depends on the nature of the sample. The range covers at least 90 degrees (at least 45 degrees each side of a normal direction to the sample). For the arch which is intended to surround a sample, the angular range approaches 180 degrees. The range is shown as θ in FIG. 3, and is approximately 135 degrees in this example.

By illumination from different light sources, light can be provided at different angles spanning the range available.

Of course, light may not reach each part of the sample surface from all directions. For example the panel to the left will not be illuminate by light from the right. Thus, the light source scan the full range of angles θ but each point on the sample surface may experience a range of incident light angles which is smaller.

The multiple arches in FIG. 3 are aligned along a direction shown by arrow 30 which corresponds to a direction of relative movement between the sample and the lighting arrangement. This relative movement means that the lighting arrangement is used to enable inspection of different parts of the sample in sequence, as well as different samples in sequence.

The light sources are controlled to operate in a sequence such that each point of the sample is illuminated in a sequence with a maximum light source intensity in a single incident direction. This direction changes over time to cover the range θ.

In a simplest implementation, only one light source (or only one light source of each arch) is turned on fully at a time. In this case, the maximum illumination is the brightness of that light source, and all other light sources have a zero output.

However, FIG. 3 shows a more advanced control approach.

The timing diagram in FIG. 3 plots intensity I versus time t. It shows a sinusoidal intensity profile for the light source L1. All other light sources are controlled to provide the same period and amplitude sinusoidal intensity profile with shifted phases, as shown. Only the maxima of the intensity profiles for the light sources L2 to L9 are shown, to avoid excessively cluttering the timing diagram. The period can be of the order of seconds, for example in the range 1 s to 20 s, to provide some time for inspection with each particular directional characteristic.

At a sequence of points in time, there is one light source with maximum intensity, and all others have lower intensity, such as time $t_1$ for light source L1. At each of these time points, each point of the sample in the field of view of the light source is illuminated with a maximum light source intensity in a single incident direction. This direction evolves over time. As can be seen in FIG. 3, there are intermediate points in time when two adjacent light sources have equal (and not quite maximum) intensity. When a light source is alone in providing the maximum intensity, it source can be considered to provide a principal direction of illumination, although all other light sources (apart from any set to the minimum intensity if this minimum is zero) are contributing to the general level of illumination.

The directional intensity difference still enables enhanced shadowing and therefore improved detection of defects.

By using multiple arches, the intensity varies across not only the plane perpendicular to the motion vector 30, but also along the direction of the motion vector 30. The sequence of phase shifted sinusoidal functions creates a very smooth light distribution change in both horizontal orientations and vertical orientations. Any defect shape can be easily detected at a particular moment of time at which the directional lighting is most suitable for that particular defect.

Figure 4:
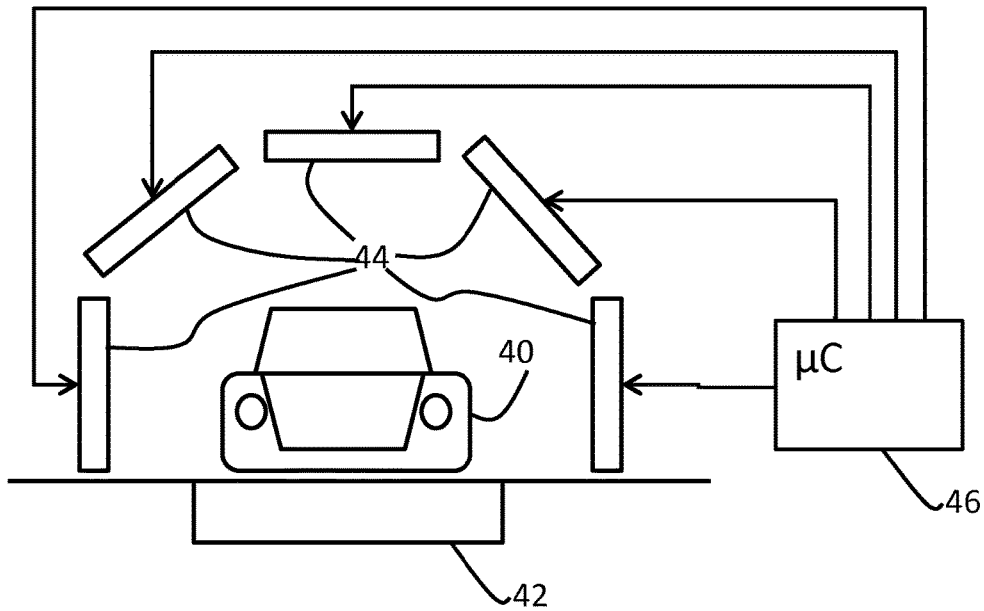
FIG. 4 shows a lighting system of the invention used in an automobile body spraying station.

FIG. 4 shows a lighting system of the invention used in an automobile body spraying station.

The vehicle body 40 is mounted on a sample platform which is movable relatively to the lighting system in a direction perpendicular to the plane (i.e. along the direction of the vector 30).

FIG. 4 shows only one arch of light sources 44. There may be only one arch or there may be multiple arches as described above.

The light sources are controlled by a controller 46 to provide the sequential control above.

The invention can be used for defect detection in welding, painting shops and assembling lines. It can enable errors to be found earlier in the manufacturing process and thereby reduce costs, by avoiding the need to repair defects later in the production cycle than necessary.

For a visual inspection system, it can simplify detection and thereby make the detection less dependent on worker experience.

There are many ways to implement the system of the invention. The concept is that there is a single direction from which a brightest illumination beam originates. By scanning this brightest illumination beam to cover the full range of angles, there will be an angle most suitable for detecting a particular defect.

As explained above, in a most simple implementation, one main light source can be turned on at a time. This means that all direct light (i.e. ignoring reflections) illuminating the part of the sample in the field of view of the light source is illuminated with a directional beam. For a point light source, this direction will be different for different points on the sample. Alternatively, a collimated light source can be used which has an output area (such as a strip), so that the incident direction is the same for all points on the sample illuminated by that light source.

Figure 5:
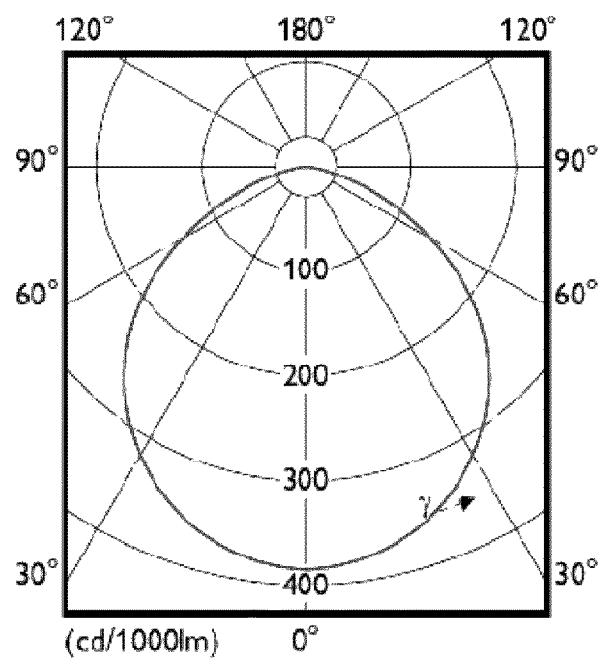
FIG. 5 shows the polar light intensity distribution for a luminaire that can be used.

Light strips for inspection are commercially available. For example, the Philips paint inspection luminaires SM300C and SM301C can be used. These comprise strip lights, with a (partially) collimated output. The light output is not perfectly collimated, in particular because the light output area from one strip needs to merge with the light output are of the next strip (along the direction of relative movement) to provide illumination of a complete task area. The luminaire has a peak intensity in a normal emission direction, but there is a spread of lower intensity light to the sides of the normal emission direction. By way of example, FIG. 5 shows the polar light intensity distribution for these strip luminaires. The narrower the beam angle, the greater the shadow effect as desired by this invention, but a larger beam angle is desired to illuminate the target area. Thus, a trade-off is found.

Thus, the invention does not require a perfectly collimated light output. Instead, there is a direction for which the illumination to a particular point on the sample has a higher intensity than for all other directions. In general, the higher intensity illumination is for the light emitted from a light source in a normal direction to the light output surface.

By operating the light sources in sequence (one at a time), each point on the sample will be illuminated from a set of incident angles in sequence, and the incident direction at which the highest intensity is received will change over time.

The example above instead operates all light sources simultaneously, but with varying intensity, so that at there is one incident direction for which the incident light has highest intensity at certain point in time, and this highest intensity light causes shadows with respect to the lower intensity illumination from other directions. This allows a more rapid inspection process, because a light source can remain with a highest intensity for a short time before the next light source in the sequence adopts the highest intensity. The minimum light source intensity can be zero but it may instead be a non-zero minimum.

The invention can be implemented as a single set of light sources (in a single plane perpendicular to the direction of relative movement of the sample). The example above makes use of multiple planes of light source arrays, again to reduce the sample inspection time.

The invention can be used to enable visual inspection of defects. However, it can also be used to provide illumination for automated defect inspection using cameras and image processing. Automated defect inspection can also be based on analysis of contrast profiles, and the lighting arrangement of the invention can thus equally improve the defection detection rate of automated defect detection systems.

In an automated defect inspection system, a set of cameras can be used to record an image sequence of the car body (or other object). For example, there may be a camera associated with each light source orientation in the arch, so that the cameras together have a field of view around the object being examined. Similar to the arches of light sources, there can be a single gantry of cameras, or there can be multiple gantries of cameras.

The lighting distribution on the car body surface is changed in the manner explained above. Image processing applied to the image sequences captured by the cameras is then used to detect changes in the recorded image sequence. These changes result from different defects being visible differently for different image lighting conditions. As explained above, the appearance of errors (scratches, humps) will change depending on the used light distribution, whereas the appearance of the error-free surfaces will remain substantially the same. As a result, analysis of the image sequence of an individual camera can be used to check whether there are significant differences in this sequence. If significant differences are detected, then it indicates existence of a defect.

Figure 6:
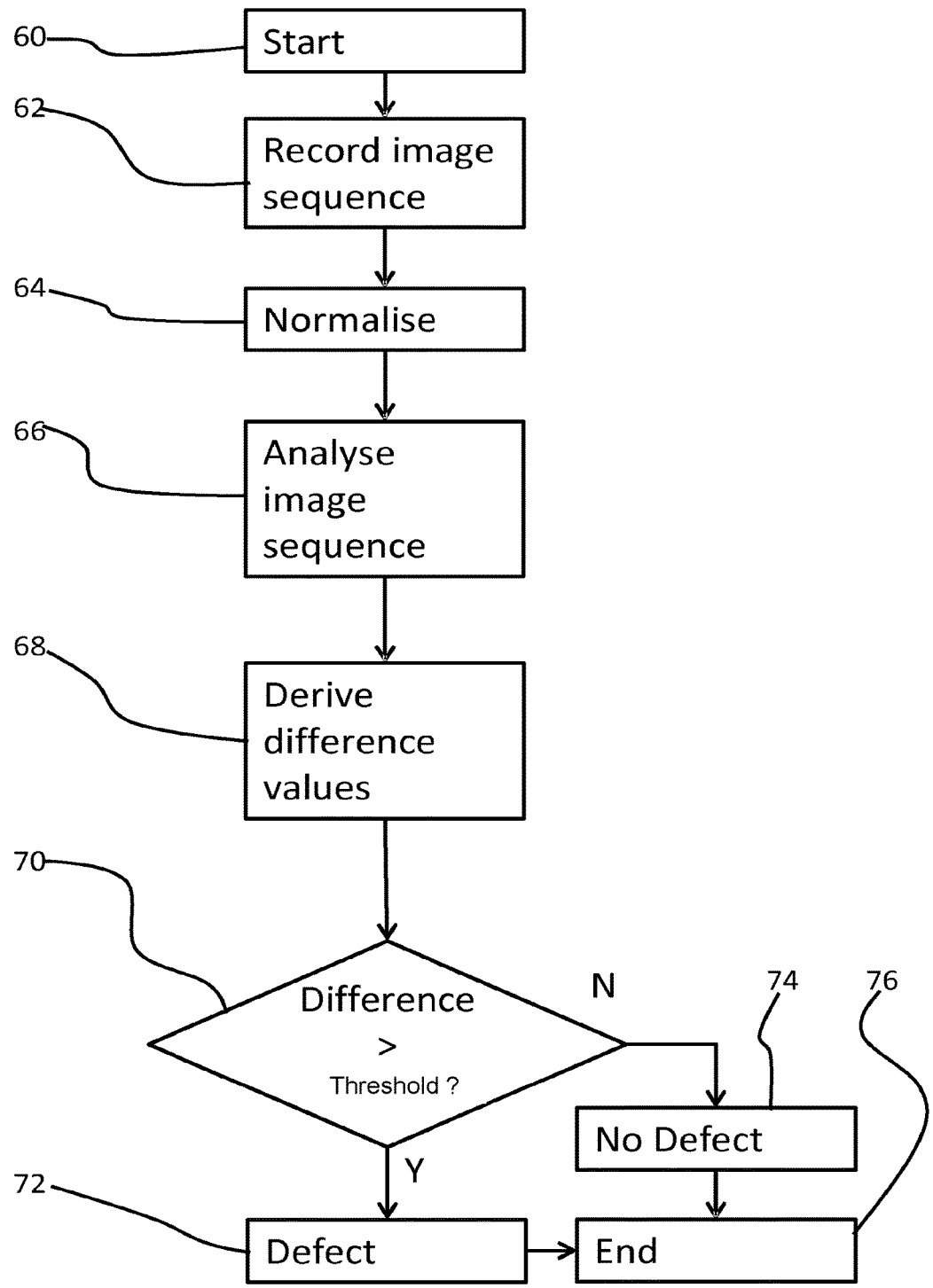
FIG. 6 is a flow chart showing an automated method of error detection using cameras.

FIG. 6 is a flow chart outlining this method of defect detection. It can be applied to each of the cameras.

The process starts in step 60. The image sequence is recorded in step 62, for at least one full cycle of lighting changes. A normalisation step is shown in step 64 to account for different light levels, for example by subtracting a median value.

The image sequence is analysed in step 64, and from this a set of difference values is derived in step 68. Each difference value is a measure of the amount of image content in a difference image. These difference values are compared with a threshold in step 70, so that if the difference between a pair of images exceeds a threshold then a defect is detected (step 72) whereas if the pair of images (or none of the multiple pairs of images analysed) produces a difference exceeding the threshold then no defect is detected (step 74). The process ends in step 76.

The difference images, and the measure of their image content, can be found by standard image processing. The number of images processed can correspond to the number of light sources, so that one image is processed when each light source is at its maximum intensity. However, not all difference images may need to be derived. For example, difference images may only be needed for light sources facing the part of the object viewed by the camera. With reference to FIG. 4, if the camera is imaging one side of the car, only the difference between images when the two light sources on that side have their maximum output may be required. Thus, in theory difference images can be analysed between all pairs of images in the sequence, but reduced image processing can be achieved if the image pairs to be processed are selected in dependence on the relative positions of the light sources and cameras. As a minimum, only one pair of images needs to analysed to derive a difference image for the camera, based on two different lighting conditions.

Figure 7:
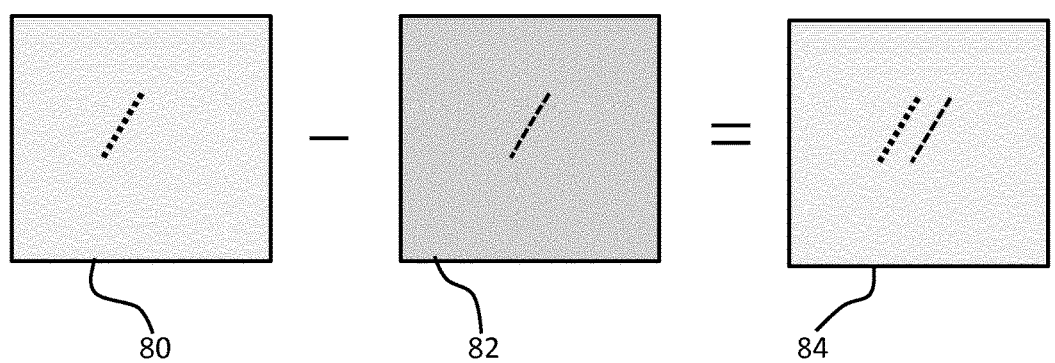
FIG. 7 shows schematically first and second camera images for different light settings and shows a difference image which enables error detection.

FIG. 7 shows schematically first and second images 80,82 for a particular camera for different light settings. A scratch is seen in each image. Because the scratch is seen as a shadow, which has a different position (and contrast) in dependence on the lighting direction, there is a difference image shown as 84.

The difference image is processed to derive an indicator of the level of image content. This can be based on the maximum brightness in the image, or the maximum difference between the darkest image area and the brightest image area. More complicated image processing can be used. The value which indicates the level of image content is then compared with a threshold. The threshold will be chosen based on the expected level for a defect-free surface, and will be different for different products being analysed.

The difference image thus highlights changes in shadow position caused by randomly located surface defects on an otherwise smooth surface.

The control of the lighting direction only applies to the light emitted from the light source, without any reflections—and this is what is meant by "direct" lighting in the discussion above. There will be other illumination caused by reflections, but this will always be of lower intensity than the direct illumination. Furthermore, the reflections can be reduced by designing the enclosure for the inspection system as non-reflecting.

The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

FIG. 3 shows an arrangement with three light sources per arch, and FIG. 4 shows five light sources per arch. The greater the number of light sources, the greater the number of different illumination directions provided. By way of example, there may be fix arches, with six luminaires per arch to cover a car. There may be much longer runs, for example for an inspection area in which multiple cars are lined up.

The invention is of particular interest for a sample which comprises a sheet material, or which has a sheet surface, which is intended to have a smooth surface (which may be a flat plane or a smoothly curved surface), but which may have randomly located surface defects at which the smoothness of the surface is disrupted. The surface may have a shaped profile, but it is intended to be smooth at the scale of the defects which are being identified. These defects may for example comprise raised bumps or dents in a painted surface, and they may for example have a scale similar to captured particles, for example less than 0.5 mm.

The system of FIG. 4 makes use of a controller. Components that may be employed for the controller include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A defect inspection system for visually inspecting surface defects in a sample, comprising:
   a lighting system for illuminating the sample surface, comprising an array of light sources, wherein the array of light sources defines a range of illumination directions towards the sample within a plane of incidence, said range covering at least 90 degrees; and
   a controller for controlling the light sources in the array to gradually vary output intensity of the light sources, wherein at respective points in time within a sequence each light source has a greater intensity than the others such that each point of the sample is illuminated, at the respective points in time within the sequence, with a light distribution having a maximum light source intensity in a single incident direction, and over time the direction in which the maximum light source intensity is provided changes to cover said range; and
   a sample platform movable relative to the lighting system within said range of illumination directions defined by said array of light sources in a direction along a line perpendicular to said plane of incidence.

2. A defect inspection system for inspecting surface defects in a sample, comprising:
   a lighting system for illuminating the sample surface, comprising an array of light sources, wherein the array of light sources defines a range of illumination directions towards the sample within a plane of incidence, said range covering at least 90 degrees; and
   a controller for controlling the light sources in the array to gradually vary output intensity of the light sources, wherein at respective points in time within a sequence each light source has a greater intensity than the others such that each point of the sample is illuminated, at the respective points in time within the sequence, with a light distribution having a maximum light source intensity in a single incident direction, and over time the direction in which the maximum light source intensity is provided changes to cover said range;
   a sample platform movable relative to the lighting system within said range of illumination directions defined by said array of light sources in a direction along a line perpendicular to said plane of incidence;
   at least one camera;
   a controller for controlling the camera to take successive images during the light source operation sequence; and
   a processor for processing the images to derive at least one difference image, wherein the difference image highlights changes in shadow position caused by randomly located surface defects on an otherwise smooth surface, and to provide defect detection based on the difference image.

3. The system as claimed in claim 1, wherein said range covers at least 135 degrees.

4. The system as claimed in claim 1, wherein the controller is adapted to control the array to vary the output intensity of the light sources with sinusoidal intensity profiles, each profile having a same period and a different phase.

5. The system as claimed in claim 1, wherein the array comprises a plurality of sub-arrays of light sources, each sub-array defining a range of illumination directions towards the sample within a respective plane of incidence, a normal direction of the respective plane of each sub-array being arranged along a same line.

6. The system as claimed in claim 1, comprising a car body panel paintwork inspection system.

7. A method of providing lighting to a surface of a sample to enable visual inspection of defects in the sample, the method comprising:
   illuminating the sample surface using an array of light sources, wherein the array of light sources defines a range of illumination directions towards the sample within a plane of incidence, said range covering at least 90 degrees;
   controlling the light sources in the array to gradually vary output intensity of the light sources, wherein at respective points in time within a sequence each light source has a greater intensity than the others such that each point of the sample is illuminated, at the respective points in time within the sequence, with a light distribution having a maximum light source intensity in a single incident direction, and over time the direction in which the maximum light source intensity is provided changes to cover said range; and
   moving the sample using a sample platform relative to the lighting system within said range of illumination directions defined by said array of light sources in a direction along a line perpendicular to said plane of incidence.

8. A method of providing lighting to a surface of a sample to enable inspection of defects in the sample, the method comprising:
   illuminating the sample surface using an array of light sources, wherein the array of light sources defines a range of illumination directions towards the sample within a plane of incidence, said range covering at least 90 degrees; and
   controlling the light sources in the array to gradually vary output intensity of the light sources, wherein at respective points in time within a sequence each light source has a greater intensity than the others such that each point of the sample is illuminated, at the respective points in time within the sequence, with a light distribution having a maximum light source intensity in a single incident direction, and over time the direction in which the maximum light source intensity is provided changes to cover said range;
   moving the sample using a sample platform relative to the lighting system within said range of illumination directions defined by said array of light sources in a direction along a line perpendicular to said plane of incidence;
   taking successive camera images during light source operation sequence;
   processing the images to derive at least one difference image wherein the difference image highlights changes in shadow position caused by randomly located surface defects on an otherwise smooth surface; and
   providing defect detection based on the difference image.

9. The method as claimed in claim 8, comprising controlling the array to vary the output intensity of the light sources with sinusoidal intensity profiles, each profile having a same period and a different phase.

10. The method as claimed in claim 8, comprising illuminating the sample using the array comprising a plurality of sub-arrays of light sources, each sub-array defining a range of illumination directions towards the sample within a respective plane of incidence, the respective planes of incidence for different sub-arrays being parallel to each other.

11. The method as claimed in claim 8, comprising controlling the light sources of the sub-arrays of light sources to illuminate the sample such that a single incident direction of maximum light source intensity in a light distribution from each sub-array of light sources within each respective plane is different for different respective planes.

12. The system as claimed in claim 5, wherein the controller is adapted to gradually vary the output intensity of the light sources from the sub-array within each respective plane of incidence in accordance with a respective sequence, wherein at respective points in time within the respective sequence, each light source from the sub-array has a greater intensity than the other light sources from the sub-array, and wherein a single incident direction of maximum light source intensity in a light distribution from each sub-array of light sources within each respective plane of incidence is different for different respective planes.

13. The system as claimed in claim 1, wherein said range covers at least 180 degrees.

* * * * *